United States Patent [19]

Papantoniou

[11] 4,047,888

[45] Sept. 13, 1977

[54] HAIR DYE COMPOSITION CONTAINING A CATIONIC RESIN

[75] Inventor: Christos Papantoniou, Epinay-sur-Seine, France

[73] Assignee: L'Oreal, Paris, France

[21] Appl. No.: 690,783

[22] Filed: May 27, 1976

[30] Foreign Application Priority Data

May 28, 1975 Luxembourg .............................. 72592

[51] Int. Cl.² .............................................. A61K 7/13
[52] U.S. Cl. ............................................ 8/10.2; 8/10; 8/11; 8/32; 8/87; 424/DIG. 2; 424/70
[58] Field of Search ................... 8/10, 10.1, 10.2, 11, 8/32, 87; 424/70

[56] References Cited

U.S. PATENT DOCUMENTS

| | | | |
|---|---|---|---|
| 3,912,808 | 10/1975 | Sokol | 8/10.2 X |
| 3,973,901 | 8/1976 | Micchelli et al. | 8/10.1 |

Primary Examiner—Albert T. Meyers
Assistant Examiner—Vera C. Clarke
Attorney, Agent, or Firm—Cushman, Darby & Cushman

[57] ABSTRACT

A hair dye composition comprises in a cream or gel vehicle or support at least one oxidation dye and at least one graft cationic copolymer of N-vinylpyrrolidone, dimethylaminoethyl methacrylate and polyethylene glycol.

10 Claims, No Drawings

HAIR DYE COMPOSITION CONTAINING A CATIONIC RESIN

The present invention relates to a new cosmetic composition for dyeing living human hair, as well as to a process for dyeing the hair using the said composition.

Various well known and currently employed hair dye compositions often leave the hair lusterless and hard. In an effort to overcome these disadvantages, it has been proposed to treat the hair with conditioners, principally cationic products, which are applied to the hair after a dyeing operation and before the final setting of the hair.

However, it has been established that this supplemental step in the process of dyeing hair also presents certain disadvantages and does not necessarily impart good cosmetic properties to the hair.

It has now been found that it is possible to impart to the hair its original appearance while improving its luster and its softness to the touch by using a composition for dyeing the hair which contains a cationic resin of a particular type.

Thus, the present invention relates to a new composition for dyeing the hair comprising in a carrier in the form of a cream or gel at least one oxidation dye and at least one graft cationic copolymer, the said copolymer resulting from the copolymerization of:
a. N-vinylpyrrolidone,
b. dimethylaminoethyl methacrylate and
c. polyethylene glycol.

It has been found that the presence of this type of graft cationic copolymer significantly improves the luster, the brilliance, the feel and the untangling of the hair after a dyeing operation.

In effect, comparative tests show that when other types of cationic copolymers having a structure different from that of the cationic copolymer employed in the present invention are employed, the results obtained were considerably less favorable, notably in that which concerns the luster and the untangling of the hair.

In accordance with a particular embodiment of the present invention, the graft cationic copolymer employed is one which is quaternized with a quaternization agent selected from the group consisting of dimethyl sulfate, diethyl sulfate, benzyl chloride, benzyl iodide or benzyl bromide.

The graft cationic copolymer of the present invention consists, preferably, of:
a. 3–95 weight percent N-vinyl pyrrolidone,
b. 3 to 95 weight percent dimethylaminoethyl methacrylate, quaternized or not, and
c. 2 to 50 weight percent, preferably 5 to 30 weight percent, of polyethylene glycol.

The polyethylene glycol employed in the production of the graft cationic polymer of the present invention has, generally, a molecular weight between 200 and several million but preferably between 300 and 30,000, while the graft cationic copolymer, as defined above, has a molecular weight between 10,000 and 1,000,000 and preferably between 15,000 and 500,000.

It has been found that excellent results are obtained when the dye composition of the present invention contains said graft cationic copolymer in an amount between 0.5 and 5 weight percent relative to the total weight of the dye composition.

In a preferred embodiment of the present invention, the composition is prepared at the moment of use, i.e. the graft cationic copolymer is added either alone or in solution in a solvent for the dye composition to the remaining components of said composition.

In accordance with yet another preferred embodiment of the present invention, the composition is provided in the form of a two-part conditioner, the first part comprising the said remaining dye composition components and the second part comprising the said graft cationic copolymer either alone or in solution in a solvent.

Preferably, the graft cationic polymer is in an aqueous solution containing or not a solvent such as ethyl alcohol, isopropyl alcohol, butyl Cellosolve (2-butoxy ethanol), ethyl Cellosolve (2-ethoxy ethanol), methyl Cellosolve (2-methoxy ethanol) or propylene glycol.

These graft cationic polymer solutions can also contain conventional cosmetic adjuvants such as thickening agents, protein hydrolyzates or certain dyes, the pH of these solutions being generally close to neutrality.

The oxidation dye is present in the dye composition of the invention in an amount ranging between about 0.006 and 6 weight percent thereof. Representative oxidation dyes include, for instance, paraphenylene diamine, orthophenylene diamine, paratoluylene diamine, methoxy paraphenylene diamine, chloroparaphenylene diamine, 2,6-dimethyl paraphenylene diamine, 2,5-dimethyl paraphenylene diamine, 2-methyl-5-methoxy paraphenylene diamine, 2,6-dimethyl-5-methoxy paraphenylene diamine, N,N-dimethyl paraphenylene diamine, 3-methyl-4-amino-N,N-(diethyl)aniline, N,N-(di-$\beta$-hydroxyethyl) paraphenylene diamine, 3-methyl-4-amino-N,N-(di-$\beta$-hydroxyethyl) aniline, 3-chloro-4-amino-N,N-(di-$\beta$-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl, morpholinoethyl)aniline, 3-methyl-4-amino-N,N-(ethyl, morpholinoethyl)aniline, 4-amino-N,N-(ethyl, acetylaminoethyl) aniline, 3-methyl-4-amino-N,N-(ethyl, acetylaminoethyl)aniline, 4-amino-N,N-(ethyl, mesylaminoethyl)aniline, 3-methyl-4-amino-N,N-(ethyl, mesylaminoethyl)aniline, 4-amino-N,N-(ethyl, $\beta$-sulfoethyl)aniline, 3-methyl-4-amino-N,N-(ethyl, $\beta$-sulfoethyl) aniline, N-[(4'-amino)phenyl]morpholine, N-[(4'-amino)phenyl] piperidine, 4-amino-N,N-(ethyl, piperidinoethyl)aniline, 3-methyl-4-amino-N-methyl aniline, 2-chloro-4-amino-N,N-(ethyl, sulfonamidomethyl)aniline, 2-chloro-4-amino-N-(ethyl)aniline, 2-methyl-4-amino-N-($\beta$-hydroxyethyl)aniline, paraamino diphenylamine, paraamino phenol, 2-methyl-4-amino phenol, 3-methyl-4-amino phenol, 2-chloro-4-amino phenol, 3-chloro-4-amino phenol, 2,6-dimethyl-4-amino phenol, 3,5-dimethyl-4-amino phenol, 2,3-dimethyl-4-amino phenol, 2,5-dimethyl-4-amino phenol, 2,5-diamino pyridine, 2-dimethyl amino-5-amino pyridine, 2-diethylamino-5-amino pyridine, 3-methyl-7-amino phenomorpholine, 5-amino indole, N-methyl paraamino phenol and ortho amino phenol, of a salt of said compound, for example a mono-, di- or tri-hydrochloride, or hydrobromide or even a sulfate thereof.

The oxidation dye, either alone, but most often in admixture, can also be combined with a coupler in an amount between 0.002 to 4 weight percent, or with a direct dye in an amount between 0.002 to 4 weight percent, or even in admixture with a coupler and a direct dye, each in amounts as set forth above.

Representative couplers include, for instance, resorcinol, meta-amino phenol, 2,4-diamino anisol, 2-methyl-5-ureido phenol, 2,6-dimethyl-3-amino phenol, 2-methyl-5-acetylamino phenol, 2,6-dimethyl-5-acetylamino phenol, 3-amino-4-methoxy phenol, 2-methyl-5-N-β-hydroxyethylamino phenol, meta phenylene diamine, meta toluylene diamine, pyrocatechol, hydroquinone, 1'α-naphthol, 1,5-dihydroxynaphthalene, 2,6-diamino pyridine, N-methyl meta amino phenol, 6-methyl-3-amino phenol, 6-hydroxy phenomorpholine and pyrazolonic couplers such as 1-phenyl-3-methyl pyrazolone-5 or a salt of said compounds, such compounds, such as the mono-, di- or tri-hydrochloride, or hydrobromide or sulfate thereof.

Representative direct dyes include, for instance, azo dyes, anthraquinone dyes, indamines, indoanilines, indophenols and their derivatives as well as nitro-benzene dyes and most particularly compounds having the formula

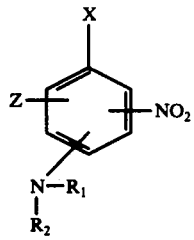

wherein

X represents hydrogen, a halogen such as Cl, Br or F, alkyl having 1-5 carbon atoms,

or $-OR_5$, wherein $R_1$, $R_2$, $R_3$, $R_4$ and $R_5$ each independently represent hydrogen, linear or branched alkyl, hydroxy alkyl, amino alkyl, acylamino alkyl, carbethoxyamino alkyl, ureidoalkyl, carboxy alkyl, sulfoalkyl, carbamyl alkyl, methoxy alkyl and mesylamino alkyl, wherein each of said alkyl moieties contains 1-5 carbon atoms and Z reprsents hydrogen, halogen, alkyl, alkoxy or nitro, wherein each of said alkyl and alkoxy moieties contains 1-5 carbon atoms.

The dye carrier or vehicle employed in accordance with the present invention can be a conventional carrier or support, but it is preferably, as indicated above, a cream or a gel.

When the carrier of the dye is present in the form of a cream, the different components constituting it are preferably provided in the following weight percent amounts:

| Fatty alcohols | 10–30% |
| --- | --- |
| Alkyl sulfates, oxyethylenated or not | 2 to 20% |
| Fatty amides | 0 to 30% |
| Water, q.s.p. | 100% |

The above percentages are expressed relative to the total weight of the dye composition.

Representative fatty alcohols include, for instance, cetylstearyl alcohol, oleyl alcohol, lauryl alcohol, isostearyl alcohol and synthetic fatty alcohols having from 9-20 carbon atoms.

Representative useful alkyl sulfates include, for instance, sodium lauryl sulfate, sodium cetylstearyl sulfate, triethanolamine cetylstearyl sulfate, triethanolamine lauryl myristyl sulfate, monoethanolamine lauryl sulfate, sodium lauryl ether sulfate oxyethylenated with 2.2 moles of ethylene oxide and monoethanolamine lauryl ether sulfate oxyethylenated with 2.2 mols of ethylene oxide.

Representative fatty amides include, for instance, the mono- or diethanolamides of the fatty acids of copra or the diethanolamides of oleic acid.

When the carrier for the dye is present in the form of a gel, the different essential components constituting it are preferably provided in the following weight percent amounts:

| Nonionic compounds, oxyethylenated or polyglycerolated | 10–60% |
| --- | --- |
| Solvent - alcohols or glycols | 5–30% |
| Fatty amides | 0–30% |
| Water, q.s.p. | 100% |

The above percentages are expressed relative to the total weight of the dye composition.

Representative oxyethylenated or polyglycerolated nonionic compounds include, for instance, nonyl phenol oxyethylenated with 4 or 9 moles of ethylene oxide, oleyl alcohol polyglycerolated with 2 or 4 moles of glycerol, cetylstearyl alcohol polyglycerolated with 2 or 6 moles of glycerol and synthetic fatty alcohols containing 11–15 carbon atoms, oxyethylenated with 3–10 moles of ethylene oxide.

Representative solvents include, for instance, lower aliphatic alcohols such as ethyl alcohol, propyl alcohol or isopropyl alcohol; glycols such as propylene glycol, butyl glycol or cellosolve.

Representative fatty amides useful in these gels include those set forth in describing the cream form composition of the present invention.

However, these two types of supports can also contain other conventional components such as, for example, perfumes, fatty acids, hair restructuring agents, stabilizers, anti-oxidants and the like. The pH of these supports containing one or more solvents is generally between 9 and 11 and is obtained by the addition thereto of an appropriate base in the dye carrier, for example, ammonia, monoethanolamine, diethanolamine or triethanolamine.

The present invention also relates to a process for dyeing living human hair comprising admixing said composition in accordance with the invention at the moment of use with an appropriate amount of $H_2O_2$, applying the resulting admixture to the hair, permitting said admixture to remain in contact with the hair for 5 to 40 minutes and then rinsing the hair.

Generally, the amount of $H_2O_2$, generally a 6 or 9% solution thereof, admixed with the dye composition, is between 50 and 75 weight percent relative to the weight of the dye composition. Hair treated in accordance with this process is easily untangled and has a silky touch.

In accordance with a particular embodiment of the present invention, the hair dyeing operation is immediately followed by a hair setting operation so as to impart to the hair a desired configuration or wave.

The graft cationic copolymers employed in accordance with the present invention are obtained by a polymerization reaction which can be carried out in accordance with known methods, i.e. in mass, in suspension, in emulsion or in solution in a solvent. In a preferred manner, the polymerization is carried out in solution.

Initiators employed in this polymerization reaction generally are classic radical polymerization initiators. Representative initiators usefully employed include, for instance, peroxides such as benzoyl peroxide, lauroyl peroxide, acetyl peroxide and benzoyl hydroperoxide.

A polymerization catalyst can also be employed. Generally these catalysts are those which on decomposition evolve an inert gas. Representative catalysts include azobisisobutyronitrile.

The concentration of the initiator is generally between 0.2 and 15 weight percent and preferably between 0.5 and 12 weight percent relative to the total weight of the polymerization reactants.

The molecular weight of the graft cationic copolymer can be regulated by introducing during the course of the polymerization small amounts of chain regulating agents such as an aldehyde, for instance, butyraldehyde or a halogenated compound such as chloroform, bromoform, carbon tetrachloride, or a mercaptan, such as lauryl mercaptan, and the like.

The following non-limiting examples are provided to illustrate the present invention.

EXAMPLES FOR PREPARING GRAFT CATIONIC COPOLYMERS

EXAMPLE 1

Into a 500 ml round bottomed flask, provided with a mechanical stirrer, a condenser, and a thermometer, there are introduced the following reactants:

| | |
|---|---|
| N-vinylpyrrolidone, freshly distilled | 50.6 g |
| Dimethylaminoethyl methacrylate, quaternized with dimethyl sulfate | 41.25 g |
| Polyethylene glycol, MW-20,000 | 8.15 g |
| Azo-bis-isobutyronitrile | 0.2 g |
| Ethanol, absolute | 20 g |

The reaction mixture is heated with agitation to 65° C. When the reaction mixture becomes viscous, an additional 80 g of absolute ethanol previously heated to 65° C are added. The temperature is then raised and held constant at about 76° C and the agitation is continued for 24 hours.

After this period of time, 200 g of water are introduced into the reaction medium and the water-ethanol azeotrope is distilled until all of the ethanol is eliminated.

There is thus obtained a yield of 98% of the desired polymer, which has a viscosity of 32 cps, measured in a 2% solution of the polymer in water at a temperature of 34.6° C.

EXAMPLE 2

Into a 500 ml round bottomed flask fitted with a mechanical stirrer, a condenser and a thermometer, there are introduced the following reactants:

| | |
|---|---|
| N-vinylpyrrolidone, freshly distilled | 54.62 g |
| Dimethylaminoethyl methacrylate | 9.87 g |
| Polyethylene glycol, MW-20,000 | 8.81 g |
| Azo-bis-isobutyronitrile | 0.2 g |
| Ethanol, absolute | 20 g |

By operating in the manner set forth in Example 1, there is thus obtained a graft cationic copolymer in a yield of 98%, said polymer having a viscosity of 11.2 cps. measured in a 2% solution of the polymer in water at a temperature of 34.6° C.

EXAMPLE 3

Into a 3 liter round bottomed flask, fitted with a mechanical stirrer and a thermometer, there are introduced the following reactants:

| | |
|---|---|
| N-vinylpyrrolidone | 303.6 g |
| Polyethylene glycol (MW-20,000) | 48.9 g |
| Dimethylaminoethyl methacrylate, quaternized with dimethyl sulfate | 247.5 g |
| Azo-bis-isobutyronitrile | 12 g |

The temperature of this reaction mixture is rapidly elevated to 60° C at which point reaction begins and continues During the reaction, the temperature rises to 95°–100° C in about 8–12 minutes.

During this phase, a significant thickening of the reaction mass occurs. The temperature of the reaction mass is maintained at 90° C for 1 hour after the exothermicity has terminated, at which time analysis reveals a reaction rate for each of the monomers greater than 99%. The product obtained which is colorless and perfectly water soluble, has a viscosity, measured in a 2% aqueous solution of the polymer, at 34.6° C, between 22 and 28 cps.

EXAMPLE 4

Into a 500 ml round bottomed flask, fitted with a mechanical stirrer, a condenser and a thermometer, the following reactants are introduced:

| | |
|---|---|
| N-vinylpyrrolidone, freshly distilled | 50.6 g |
| Dimethylaminoethyl methacrylate | 41.25 g |
| Polyethylene glycol, MW-20,000 | 8.15 g |
| Azo-bis-isobutyronitrile | 0.2 g |
| Ethanol, absolute | 100 g |

The reaction mixture is heated to 65° C for 4 hours and then at 80° C for 20 hours. Thereafter, 200 g of water are introduced into the reaction and the water-ethanol azeotrope is distilled until all of the ethanol is eliminated. There is thus obtained a 97% yield of the desired polymer, having a viscosity of 12.45 cps, measured in a 2% solution of the polymer in water at a temperature of 34.6° C.

EXAMPLE 5

Into a 500 ml round bottomed flask fitted with a mechanical stirrer, a condenser, a thermometer and a nitrogen lead-in tube, the following reactants are introduced:

| | |
|---|---|
| N-vinylpyrrolidone, freshly distilled | 50.6 g |
| Dimethylaminoethyl methacrylate | 41.25 g |
| Polyethylene glycol, MW-20,000 | 8.15 g |
| Water | 100 g |

The mixture is heated with agitation at 40° C until the polyethylene glycol is completely dissolved. There is then introduced sufficient borax ($Na_2B_4O_7 \cdot 10H_2O$) to adjust the pH thereof to 9. Thereafter 1 ml of $H_2O_2$ (30%) is introduced and heating of the reaction mixture is maintained at 40° C for 12 hours.

The solution at the end of the polymerization is viscous but stirrable, providing a 98% of the polymer having a viscosity of 8.46 cps measured in a 2% solution in water at 34.6° C.

EXAMPLES OF COMPOSITIONS

EXAMPLE A

A hair dye composition in the form of a gel is prepared by admixing at the moment of use an aqueous solution of a graft copolymer with a dye support, in the form of a gel, containing the said hair dyes. There is thus obtained a dye composition having the following amounts of the various below listed components:

| | | |
|---|---|---|
| Nonyl phenol oxyethylenated with 4 moles of ethylene oxide | 24 | g |
| Nonyl phenol oxyethylenated with 9 moles of ethylene oxide | 23 | g |
| Ethyl alcohol (96° titer) | 7 | g |
| Propylene glycol | 14 | g |
| Ammonia (22° Be) | 10 | ml |
| Paraamino phenol, base | 0.087 | g |
| 2,4-diamino anisol sulfate | 0.03 | g |
| Resorcinol | 0.4 | g |
| Meta-amino phenol (base) | 0.15 | g |
| Nitro paraphenylene diamine | 1 | g |
| Paratoluylene diamine | 1 | g |
| Ethylene diamine tetra-acetic acid | 0.3 | g |
| Sodium bisulfite (d=1.32) | 1.2 | g |
| Graft copolymer obtained in accordance with Example 1 | 4.8 | g |
| Water, q.s.p. | 100 | g |

To 50 g of this dye composition thus obtained 50 g of $H_2O_2$ (20 volumes) are added and the resulting admixture is applied to the hair with the aid of a brush.

After permitting this admixture to remain in contact with the hair thus treated for 30 minutes, the hair is then rinsed. The thus treated hair is easily combed and has a particularly silky feel.

The hair, after being set and dried in a conventional manner, is shiny, lively, has body, has a silky feel and combs easily. On brown hair, there is obtained a chestnut coloration.

EXAMPLE B

A dye composition in the form of a gel is obtained by mixing at the moment of use an aqueous solution of the graft copolymer with a dye support, in the form of a gel, containing the hair dyes. There is thus obtained a dye composition in accordance with the invention having the following amounts of the various below listed components:

| | | |
|---|---|---|
| Oleyl alcohol glycerolated with 2 moles of glycerol | 20 | g |
| Oleyl alcohol glycerolated with 4 moles of glycerol | 20 | g |
| Butyl glycol | 8 | g |
| Propylene glycol | 12 | g |
| Ammonia (22° Be) | 10 | ml |
| Paraamino phenol (base) | 0.08 | g |
| 2,4-diamino anisol sulfate | 0.025 | g |
| Resorcinol | 0.3 | g |
| Meta-amino phenol (base) | 0.06 | g |
| Nitro-paraphenylene diamine | 0.003 | g |
| Para-toluylene diamine | 1.05 | g |
| Hydroquinone | 0.17 | g |
| Ethylene diamine tetra-acetic acid | 0.3 | g |
| Sodium bisulfite (d=1.32) | 0.8 | g |
| Graft copolymer, obtained in accordance with Example 2 | 3.5 | g |
| Water, q.s.p. | 100 | g |

To 50 g of this dye composition there are added 50 g of $H_2O_2$ (20 volumes) and the resulting admixture is applied to hair with a brush.

After permitting this admixture to remain in contact with the hair for 30 minutes, the hair is then rinsed. The thus treated hair is easily combed, has considerable body, is shiny and has a silky touch. On deep chestnut hair, there is obtained a light chestnut coloration.

EXAMPLE C

A dye composition in the form of a cream is obtained by mixing at the moment of use an aqueous solution of a graft copolymer with a dye support in the form of a cream, containing the hair dyes. There is thus obtained a dye composition in accordance with the invention having the following amounts of the various below listed components:

| | | |
|---|---|---|
| Cetylstearyl alcohol | 22 | g |
| Oleic diethanolamide | 5 | g |
| Sodium cetylstearyl sulfate | 4 | g |
| Ammonia (22° Be) | 11 | ml |
| 2,4-diaminoanisol sulfate | 0.048 | g |
| Resorcinol | 0.420 | g |
| Meta-amino phenol (base) | 0.150 | g |
| Nitro-paraphenylene diamine | 0.085 | g |
| Para-toluylene diamine | 0.004 | g |
| Ethylenediamine tetra-acetic acid | 0.2 | g |
| Sodium bisulfite (d=1.32) | 1.2 | g |
| Graft copolymer obtained in accordance with Example 3 | 4.5 | g |
| Water, q.s.p. | 100 | g |

To 30 g of this dye composition there are added 45 g of $H_2O_2$ (20 volumes). The resulting admixture is a smooth, thick cream which is pleasant to apply to the hair and which adheres well thereto.

This cream is then applied to the hair with a brush and is permitted to remain in contact therewith for 30 minutes. Thereafter the hair is rinsed.

The hair thus treated combs easily and has a silky feel.

After setting and drying the hair in a conventional manner, the hair is shiny, lively, has body, has a silky feel and is easily combed. On 100% white hair, there is obtained a blond coloration.

In this example, the copolymer of Example 3 is advantageously replaced by the copolymer of Examples 4 or 5, with equally favorable results.

The dye compositions of the present invention in the form of a cream can be obtained by using the various components below in the indicated amounts, the graft cationic copolymer as in the preceding examples being added in the form of an aqueous solution at the moment of use.

| | |
|---|---|
| Cetylstearyl alcohol | 25 to 30 g |
| Sodium cetylstearyl sulfate | 5 to 7 g |
| Ammonia (22° Be) | 13 ml |
| 2,4-diamino anisol sulfate | 0.01 to 0.25 g |
| Resorcinol | 0.13 to 0.60 g |
| M-amino phenol | 0.01 to 0.15 g |
| Nitro-p-phenylene diamine | 0.004 to 0.08 g |
| P-toluylene diamine | 0.04 to 4.50 g |
| P-amino phenol | 0.10 to 2.80 g |
| Ethylenediamine tetra-acetic acid | 0.2 g |
| Sodium bisulfite (d=1.32) | 1.20 g |
| Copolymer in accordance with Examples 1-5 | 1 to 4 g |

| -continued | |
|---|---|
| Water, q.s.p. | 100 g |

To 30 g of the dye composition above, 45 g of H₂O₂ (20 volumes) are added and the resulting admixture is applied to hair with a brush.

This admixture is permitted to remain in contact with the hair for 30 minutes, after which the hair is rinsed. The hair thus treated combs easily and has a silky touch. After setting and drying the hair, the hair is shiny, lively, has body, has a pleasant soft and silky touch and combs easily.

The use of dyes in the amounts indicated confers to the hair thus treated, as a function of its original color, shades ranging from light blond to black.

What is claimed is:

1. A hair dye composition comprising a hair dye support in the form of a cream or gel, at least one oxidation dye in an amount between 0.006 and 6 percent by weight relative to the total weight of said composition and at least one graft cationic copolymer of:
   a. 3–95 weight percent N-vinylpyrrolidone,
   b. 3–95 weight percent dimethylaminoethyl methacrylate and
   c. 2–50 weight percent polyethylene glycol,
   said graft cationic copolymer being present in an amount between 0.5 and 5 percent by weight based on the total weight of said composition and having a molecular weight between 10,000 and 100,000.

2. The composition of claim 1 wherein said hair dye support is in the form of a gel and comprises
   10–60 weight percent of a member selected from the group consisting of nonyl phenol oxyethylenated with 4 or 9 moles of ethylene oxide, oleyl alcohol polyglycerolated with 2 or 4 moles of glycerol, cetyl stearyl alcohol polyglycerolated with 2 or 6 moles of glycerol and snythetic fatty alcohols containing 11–15 carbon atoms oxyethylenated with 3–10 moles of ethylene oxide;
   5–30 weight percent of an alcohol or a glycol, as a solvent;
   0–30 weight percent of a fatty amide; and the remainder being water.

3. The composition of claim 1 wherein said graft cationic copolymer is quaternized with a quaternization agent selected from the group consisting of dimethyl sulfate, diethyl sulfate, benzyl chloride, benzyl iodide and benzyl bromide.

4. The composition of claim 1 wherein said graft cationic component has a molecular weight between 15,000 and 500,000.

5. The composition of claim 1 which also includes a coupler in an amount between 0.002 to 4 percent by weight based on the total weight of said composition.

6. The composition of claim 1 which also includes a direct dye in an amount between 0.002 and 4 percent by weight based on the total weight of said composition.

7. The composition of claim 1 wherein said dye support comprises
   10–30 weight percent of a fatty alcohol;
   2–20 weight percent of an alkyl sulfate or an oxyethylenated alkyl sulfate;
   0–30 weight percent of a fatty amide and the remainder being water.

8. The composition of claim 1 having a pH between 9 and 11.

9. The composition of claim 8 which also includes a sufficient amount of a base selected from the group consisting of ammonia, momoethanolamine, diethanolamine and triethanolamine so that said composition has said pH value.

10. A process for dyeing hair comprising applying to the hair an effective amount of the composition of claim 1 together with a sufficient amount of H₂O₂, permitting said composition to remain in contact with said hair for 5–40 minutes and rinsing said hair.

* * * * *